US00PP29941P3

(12) United States Plant Patent
LaBonte et al.

(10) Patent No.: US PP29,941 P3
(45) Date of Patent: Dec. 4, 2018

(54) SWEETPOTATO PLANT NAMED 'V12B.445'

(50) Latin Name: ***Ipomoea batatas* (L.) Lam.**
Varietal Denomination: V12B.445

(71) Applicant: Board of Supervisors of Louisiana State University and A&M College Through the LSU AgCenter, Baton Rouge, LA (US)

(72) Inventors: Don R. LaBonte, Baton Rouge, LA (US); Christopher A. Clark, Baton Rouge, LA (US); Valerio Primomo, Toronto (CA)

(73) Assignee: Board of Supervisors of Louisiana State University and Agricultural and Mechanical College Through The LSU AgCenter, Baton Rouge, LA (US)

( * ) Notice: Subject to any disclaimer, the term of this patent is extended or adjusted under 35 U.S.C. 154(b) by 69 days.

(21) Appl. No.: 15/330,638

(22) Filed: Oct. 20, 2016

(65) Prior Publication Data
US 2018/0116086 P1 Apr. 26, 2018

(51) Int. Cl.
*A01H 5/12* (2018.01)
*A01H 5/06* (2018.01)

(52) U.S. Cl.
USPC ..... Plt./258
CPC ..... *A01H 5/06* (2013.01)

(58) Field of Classification Search
USPC ..... Plt./258
See application file for complete search history.

*Primary Examiner* — Anne Marie Grunberg
(74) *Attorney, Agent, or Firm* — James C. Carver

(57) ABSTRACT

A new variety of sweetpotato, identified as 'V12B.445', is disclosed having disease resistance to both fusarium wilt and *Streptomyces* soil rot; an orange flesh and purple-red skin, and high yield characteristics.

3 Drawing Sheets

This invention pertains to a new and distinct variety of sweetpotato.

BACKGROUND OF THE INVENTION

Sweetpotatoes, unlike irish potatoes (*solanum tuberosum*), are not tuber propagated plants. A "tuber" is a short, thickened portion of an underground branch. Along a tuber, "eyes" are found, each of which comprises a ridge bearing a scale-like leaf (analogous to a branch leaf) having minute meristematic buds in the axial of the leaf. By contrast, sweetpotato roots are developmentally and anatomically true roots, lacking meristematic buds, and are not derived from an underground branch. Sweetpotatoes do not form tubers.

SUMMARY OF THE INVENTION

Genus and species name: This new and distinct sweetpotato variety, *Ipomoea batatas* (L.) Lam., demonstrates superior disease resistance to fusarium wilt and exhibits an orange flesh. It also demonstrates a purple-red skin in comparison to '05-111' with a light to medium rose skin.

Variety denomination: This new and distinct sweetpotato variety is identified as 'V12B.445', and is characterized by an orange flesh, high yield in northern latitudes, consistent shape, and a purple-red skin.

BRIEF DESCRIPTION OF THE DRAWINGS

The file of this patent contains at least one photograph executed in color. Copies of this patent or patent application with color drawing(s) will be provided by the Patent and Trademark Office upon request and payment of the necessary fee.

DETAILED BOTANICAL DESCRIPTION

This new variety of sweetpotato, named 'V12B.445', resulted from an open pollinated cross performed in 2012 to the female parent 'LA07-190' (unpatented). The male parent was unknown. Five patented male parents ('05-111' patented U.S. Plant Pat. No. 23,761 P3; 'Evangeline' patented U.S. Plant Pat. No. 19,710 P3; 'Bonita' patented U.S. Plant Pat. No. 22,719 P3; 'LA06-52' patented U.S. Plant Pat. No. 26,735 P3; and 'LA07-146' U.S. Plant Pat. No. 23,785 P3) were among the potential pollen sources in the crossing nursery. 'V12B.445' was developed to provide a variety with characteristics similar to '05-111', but with a purple-red skin and high yield in northern latitudes.

Plants of 'V12B.445' and variety '05-111' can be differentiated. Abaxial veins of 'V12B.445' are red [2.5 R (red) P (purple) (2/6)]. '05-111' has no red hue to veins. Roots of 'V12B.445' are red-purple and can be differentiated from the rose roots of the female parent 'LA07-190'. Color terminology used herein is in accordance with the MUNSELL® Book of Color (Munsell Color, GretagMacbeth LLC, 617 Little Britain Road, New Windsor, N.Y. 12553-6148). The color descriptions and color illustrations are as nearly true as is reasonably possible. However, it is understood that both color and other phenotypic expressions described herein may vary from plant to plant with differences in growth, environment and cultural conditions, without any change in the genotype of the variety 'V12B.445'.

'V12B.445' roots were stored during the winter at Vineland Station, Ontario, Canada. These 'V12B.445' roots were planted the following spring, resulting in approximately 8-10 sprouts per root. Cuttings from the sprouts were transplanted successfully for asexual reproduction at the Vineland Station, Ontario, Canada. Asexual propagation of the new cultivar by cuttings has shown that the unique features of this new sweetpotato were stable and that the plant reproduced true to type in successive generations of asexual propagation. Plants described herein were 90 days in age from planting in full sun field plantings.

Figure 1:
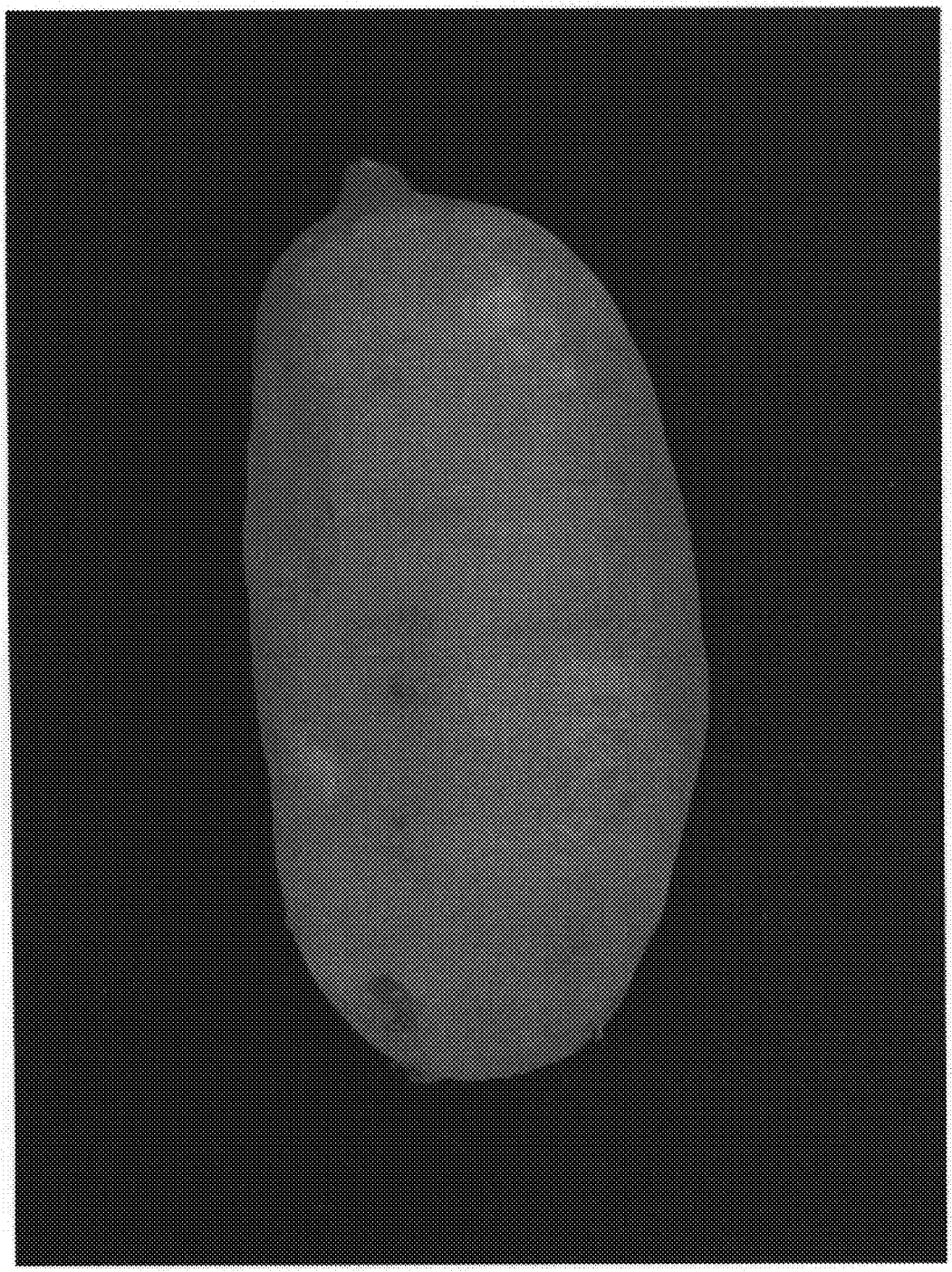
FIG. 1 is a color photograph of the fleshy root form of the novel variety of sweetpotato identified as 'V12B.445'.
Figure 2:
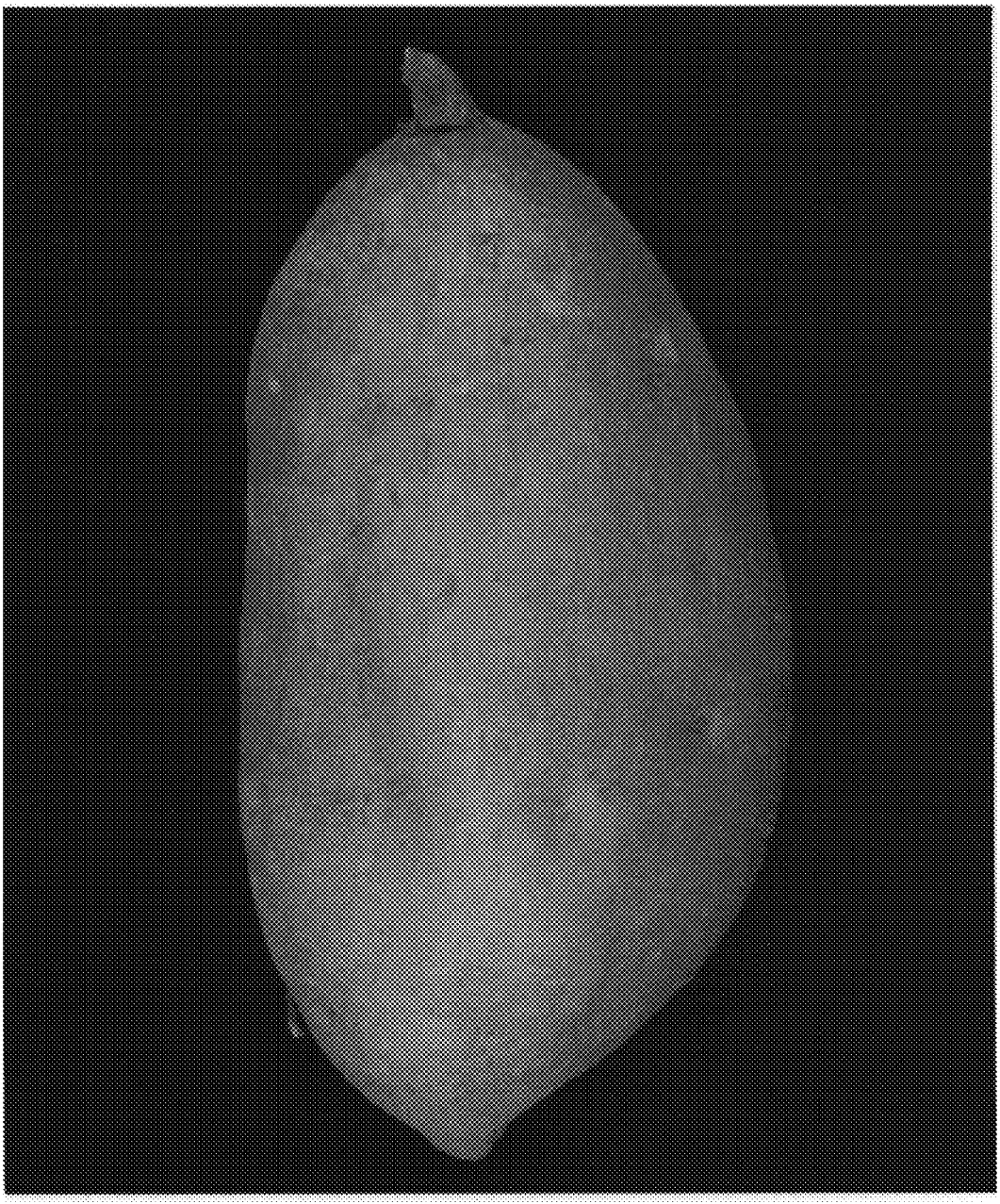
FIG. 2 is a color photograph of the fleshy root form of the sweetpotato variety identified as '05-111'.

FIG. 1 depicts the fleshy root form of the 'V12B.445' sweetpotato. The skin is red-purple and differs from the light to medium rose '05-111', both at harvest and after several months of storage as shown in Table 1. MUNSELL® Book of Color values for skin and flesh for both 'V12B.445' and '05-111' storage roots are shown in Table 1. The '05-111' sweetpotato is depicted in FIG. 2. The skin for both 'V12B.445' and '05-111' are smooth. The 'V12B.445' cortex is 4.5 mm in depth and the color is similar throughout. The flesh of 'V12B.445' is deep orange compared to the lighter flesh of '05-111'.

TABLE 1

| Variable | Variety | Color |
|---|---|---|
| Skin | 'V12B.445' | 10 R (red) 5/4 |
| | '05-111' | 2.5 Y (yellow) R (red) 6/6 |
| Flesh | 'V12B.445' | 2.5 Y (yellow) R (red) 7/10 |
| | '05-111' | 2.5 Y (yellow) R (red) 7/8 |

Figure 3:
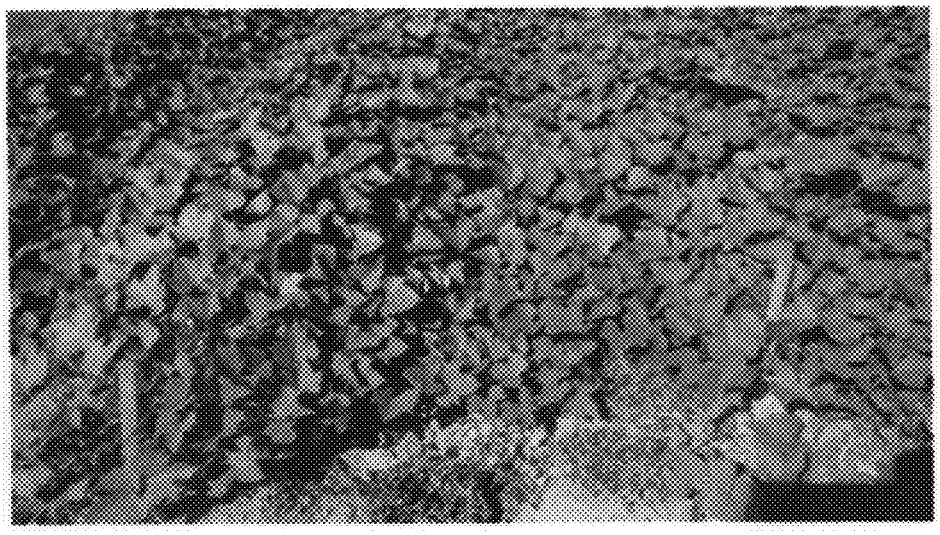
FIG. 3 is a color photograph of the canopy biomass of the novel variety of sweetpotato identified as 'V12B.445' (shown on the left side of the photograph) and '05-111' or 'Orleans' (shown on the right side of the photograph).

FIG. 3 depicts the canopy biomass of 'V12B.445' sweetpotato. Stems of 'V12B.445' are green and remain unchanged [2.5 G (green) Y (yellow) (5/8)]. The 'V12B.445' canopy biomass appears similar to '05-111'. The 'V12B.445' canopy architecture was 30 cm in height from the soil surface. For 'V12B.445', three to four main vines arose from the main stem near the soil surface. The stem giving rise to these vines was 1.1-1.4 cm in diameter; the 3-4 lateral vines were 220 cm in length with diameters of about 0.7 cm at 65 cm from the base and diameters of about 0.6 cm at the first internode of the first fully developed leaf from the apex. Three to four lateral branches arose from each of the main vines. At the first internode from the apex, the internode length was about 7 cm between the first and second fully developed leaves. Internode lengths for other sections of the vine averaged about 9 cm. Unfolded immature leaves were green [2.5 G (green) (4/6)] for the upper and lower surface, which change nominally over one to two nodes from the apex to a green upper surface [5 G (green) Y (yellow) (3/6)] to a slightly lighter green lower surface [5 G (green) Y (yellow) (5/4)]. Mature leaves at five nodes from the apex had an acute apex and mostly a cordate base and a smooth leaf margin. Mature leaves were about 11 cm long and 11 cm wide. Abaxial and ad axial veins were purple [2.5 R (red) P (purple) (4/4)]. The petiole was green [2.5 G (green) Y (yellow) (5/8)]. A red [2.5 R (red) P (purple) (4/8)] marking was at the base of the leaf junction with the petiole. The petiole was 11 cm long at five nodes from the apex, and 3.7 mm in diameter at 5 cm from the leaf junction. The dormant nodal meristem was green [2.5 G (green) Y (yellow) (5/8)].

A typical inflorescence of 'V12B.445' displayed one cluster of three flowers per peduncle. Peduncles were green [10 G (green) Y (yellow) (5/6)], about 9.1 cm long, and about 3 mm in diameter. Individual flowers were about 4.1 cm long from the base of the calyx, and the corolla was 3.6 cm wide at the opening. The fused flower petals formed a pentagonal pattern with smooth edges. The inner throat of the corolla appeared purple [2.5 R (red) P (purple) (4/10)]. The inner and outer limbs of the corolla (corollas outermost area, distal from the calyx) were light purple [10 P (purple) (8/2)]. The five sepals comprising the calyx were elliptic with a cordate apex and appeared to be green [10 G (green) Y (yellow) (6/6)]; three of these sepals were about 12 mm long and 3.8 mm wide. Two other sepals (interspersed) were about 9.4 mm long and 2.6 mm wide. Sepal margins were smooth. Stigmata were about 0.94 cm long and appeared to be purple [10 P (purple) (8/2)] at the base before fading. Five stamens were inferior to the stigmata. A slight fragrance was present.

EXAMPLE 1

Tests Conducted

To confirm that 'V12B.445' is a new variety, during 2015 and 2016 controlled tests (e.g., pathogen responses and yield) were conducted in Baton Rouge, La. 'Beauregard' and '05-111' were selected for comparison because of their importance in commercial United States orange flesh sweetpotato acreage. Diseases that commonly affect the growth of sweetpotatoes were selected to test for pathogen responses in both varieties. Scions of 'V12B.445', 'Beauregard', and '05-111' reacted similarly to most diseases evaluated in the controlled tests. 'V12B.445' was intermediate and '05-111' and 'Beauregard' were intermediate to resistant for *Streptomyces* soil rot caused by *Streptomyces ipomoeae* (Person & W. J. Martin) Waksman & Henrici. 'V12B.445', 'Beauregard', and '05-111' were resistant to *Fusarium* wilt or stem rot caused by *Fusarium oxysporum* Schlect. f.sp. *batatas* (Wollenw.) Snyd. & Hans.

Nematode reproduction was measured in greenhouse tests. 'V12B.445' was very susceptible while 'Beauregard' and '05-111' were susceptible to southern root-knot nematode, *Meloidogyne incognita* (Kofoid & White, 1919) Chitwood, 1949.

'V12B.445' has not been tested for novel insect resistance.

To determine yield production, complete-block trials using four replications of 'V12B.445', 'Covington' (Patented U.S. Plant Pat. No. 18,516), and '05-111' each were conducted in 2014 and 2015 in areas of Canada (Ontario, Manitoba, Nova Scotia, British Columbia), likely to produce 'V12B.445'. 'Covington' is included in yield estimates as it is a commercial variety grown in Canada. 'V12B.445', 'Covington', and '05-111' sweetpotato plants were transplanted in randomized complete-block trials with four replications. Plots measured 6.6 m×1.83 m and each consisted of 20 cuttings at 30 cm spacing. Field plots were prepared with a pre-emergence burnoff application of Touchdown-Total® (glyphosate acid) rototilled prior to fertilizing. The fertilizer regime was 5.6 kg/ha Solubor® (boron), 224 kg/ha 11-52-0 (N-P-K) with 13.45 kg/ha zinc sulphate. 'V12B.445' was compared to 'Covington' and '05-111' at transplanting dates as early as May 25 and late as June 12. Average yields were measured for the following grades of roots: US#1 (51-89 mm in diameter, 76-229 mm long); Canner (25-51 mm in diameter, 51-178 mm long); and Jumbo (larger than US#1 in diameter, length or both, and without objectionable defects). A typical marketable root of 'V12B.445' was mostly elliptic in shape. US#1 roots typically weigh 190 to 230 g.

'V12B.445' produced US#1 grade and total marketable yields exceeding 'Covington' in six and seven locations, respectively, out of eight environments tested in 2014 and 2015. 'V12B.445' exceeded yields of '05-111' for US#1 and total marketable yields in four and five locations, respectively, out of eight environments. Yield trials in cooler Canadian climates such as Manitoba have shown a yield decline in 'V12B.445'; however, yields were comparable to 'Covington' and '05-111'. In 2015, a yield trial in an organic type production farm has also shown a yield decline in 'V12B.445'; however, yields were higher than 'Covington' and '05-111'. 'V12B.445' produced the highest yields under black plastic mulch, which is a production system typically used in Nova Scotia and British Columbia. The yields were comparable to 'Orleans', but significantly higher than 'Covington' under these conditions. 'V12B.445' tends to have more Jumbos than 'Covington' and '05-111' indicative of its earliness. In total, these data reflect the earliness and consistent high yield characteristics for 'V12B.445'. Average yields, measured as Metric Tons per Hectare ($MT \cdot ha^{-1}$), are shown in Table 2.

TABLE 2

| Location | Year | Date Planted | Days To Harvest | Selection |
|---|---|---|---|---|
| Vineland, Ontario, CANADA | 2014 | May 29, 2014 | 133 | V12B.445<br>05-111<br>Covington |
| Vineland, Ontario, CANADA | 2014 | Jun. 12, 2014 | 126 | V12B.445<br>05-111<br>Covington |
| Simcoe, Ontario, CANADA | 2014 | Jun. 3, 2014 | 126 | V12B.445<br>05-111<br>Covington |
| Kentville, Nova Scotia, CANADA (black plastic mulch) | 2014 | Jun. 6, 2014 | 131 | V12B.445<br>05-111<br>Covington |
| Abbotsford, BC, CANADA (black plastic mulch) | 2015 | Jun. 5, 2015 | 119 | V12B.445<br>05-111 |
| Brandon, Manitoba, CANADA | 2015 | Jun. 4, 2015 | 132 | V12B.445<br>05-111 |
| Kentville, Nova Scotia, CANADA (black plastic mulch) | 2015 | May 29, 2015 | 138 | V12B.445<br>Covington |
| Round Plains, Ontario, CANADA (organic production) | 2015 | Jun. 8, 2015 | 134 | V12B.445<br>05-111<br>Covington |
| Vineland, Ontario, CANADA | 2015 | May 25, 2015 | 129 | V12B.445<br>05-111<br>Covington |
| Winkler, Manitoba, CANADA | 2015 | Jun. 5, 2015 | 123 | V12B.445<br>Covington |

| Location | US #1† | Canners† | Jumbos† | TMY†‡ |
|---|---|---|---|---|
| Vineland, Ontario, CANADA | 12.1a<br>21.1a<br>12.2a | 1.4a<br>2.6a<br>1.8a | 12.5ab<br>19.2a<br>1.4b | 26.1ab<br>42.8a<br>15.4b |
| Vineland, Ontario, CANADA | 22.2a<br>15.4ab<br>11.3b | 8.3a<br>8.5a<br>2.6a | 2.5a<br>0.5a<br>1.6a | 33.0a<br>24.4ab<br>15.5b |
| Simcoe, Ontario, CANADA | 15.2a<br>7.4a<br>6.0a | 5.8a<br>7.6a<br>9.6a | 1.4a<br>0.6a<br>0a | 22.3a<br>15.6a<br>15.6a |
| Kentville, Nova Scotia, CANADA (black plastic mulch) | 31.9a<br>33.3a<br>25.1a | 11.1a<br>11.2a<br>6.8a | 14.6a<br>0b<br>0b | 57.6a<br>44.5ab<br>31.9b |
| Abbotsford, BC, CANADA (black plastic mulch) | 26.2a<br>34.4a | 3.0a<br>6.3a | 38.7a<br>31.1a | 67.9a<br>71.8a |
| Brandon, Manitoba, CANADA | 11.1a<br>13.6a | 1.8a<br>4.2a | 2.5a<br>2.1a | 15.4a<br>19.9a |
| Kentville, Nova Scotia, CANADA (black plastic mulch) | 30.6a<br>17.7a | 1.9b<br>8.4a | 18.0a<br>1.6a | 50.6a<br>27.7b |
| Round Plains, Ontario, CANADA (organic production) | 12.2a<br>8.8a<br>8.9a | 6.6a<br>8.4a<br>7.1a | 0.2a<br>0.1a<br>0.2a | 19.0a<br>17.3a<br>16.2a |
| Vineland, Ontario, CANADA | 33.9a<br>29.2a<br>21.8a | 7.1a<br>9.3a<br>7.6a | 22.0a<br>6.6a<br>14.2a | 63.0a<br>45.1a<br>43.6a |
| Winkler, Manitoba, CANADA | 16.0a<br>17.3a | 10.9a<br>10.3a | 0.2a<br>0.6a | 27.1a<br>28.2a |

†Average Yields in $MT\text{-}ha^{-1}$ of Varieties Followed By a Common Letter Do Not Differ Significantly ($P < 0.05$) According To Tukey's Test.
TMY‡ = Total Marketable Yield Sugar profiles for raw 'V12B.445', 'Covington', and '05-111' are shown in Table 3. For 2014 and 2015 trials, roots were stored for two months after which they were prepared for sugar analysis. Glucose and fructose content in raw 'V12B.445' was higher than 'Covington' and '05-111' in both years. Sucrose and total sugar content for 'V12B.445' was higher than '05-111'. Sugar profiles for baked and fried 'V12B.445', 'Covington', and '05-111' are shown in Table 4. Sugar profiles for baked and fried 'V12B.445' were similar to '05-111' and 'Covington'. Dry matter for 'V12B.445' was lower than 'Covington' and '05-111' in both 2014 and 2015 trials and shown in Table 5. These results demonstrate differences in level of sweetness and moistness for 'V12B.445', 'Covington', and '05-111'.

TABLE 3

| Selection | Year Tested | Glucose‡ | Sucrose‡ | Fructose‡ | Total Sugars‡† |
|---|---|---|---|---|---|
| V12B.445 | 2014 | 7.07 | 5.11 | 4.41 | 16.59 |
| 05-111 | 2014 | 6.11 | 4.35 | 3.87 | 14.32 |
| Covington | 2014 | 4.62 | 9.98 | 2.67 | 17.27 |
| V12B.445 | 2015 | 6.04 | 7.00 | 3.03 | 16.14 |
| 05-111 | 2015 | 5.73 | 6.57 | 2.79 | 15.15 |
| Covington | 2015 | 4.91 | 7.62 | 2.70 | 15.29 |

†Total Sugars = Fructose + Glucose + Maltose + Sucrose
‡$mg \cdot g^{-1}$ Fresh Weight Basis

TABLE 4

| Cooking Method | Selection | Glucose‡ | Sucrose‡ | Fructose‡ | Maltose‡ | Total Sugars‡† |
|---|---|---|---|---|---|---|
| Baked | V12B.445 | 0.99 | 1.36 | 0.72 | 3.83 | 6.90 |
| | 05-111 | 0.90 | 0.98 | 0.74 | 3.90 | 6.52 |
| | Covington | 0.44 | 2.75 | 0.42 | 3.56 | 7.17 |
| Fried | V12B.445 | 1.25 | 1.32 | 1.15 | 3.92 | 7.64 |
| | 05-111 | — | — | — | — | — |
| | Covington | 1.11 | 1.03 | 1.03 | 3.88 | 7.05 |

†Total Sugars = Fructose + Glucose + Maltose + Sucrose
‡$mg \cdot g^{-1}$ Fresh Weight Basis

TABLE 5

| Selection | Year Tested | Dry Matter† |
|---|---|---|
| V12B.445 | 2014 | 16.2 |
| 05-111 | 2014 | 17.3 |
| Covington | 2014 | 19.0 |
| V12B.445 | 2015 | 18.9 |
| 05-111 | 2015 | 19.8 |
| Covington | 2015 | 20.3 |

†Dry Matter Content of Sweet Potato Lines in 2014 and 2015 Averaged Across Five and Two Locations, Respectively 'V12B.445' should be a valuable commercial sweetpotato variety. 'V12B.445' equals and often exceeds yield for US#1 and total marketable yield in comparison to '05-111' and 'Covington' in Canadian sweetpotato production regions.

We claim:

1. A new and distinct variety of *Ipomoea batatas* plant named 'V12B.445' as described and illustrated in the specification herein.

* * * * *